(12) United States Patent
Yakir

(10) Patent No.: US 7,281,926 B2
(45) Date of Patent: Oct. 16, 2007

(54) MODULAR DENTAL IMPLANTS WITH EXTENSIONS

(76) Inventor: Meir Yakir, 6571 NW. 78th Dr., Parkland, FL (US) 33067

( * ) Notice: Subject to any disclaimer, the term of this patent is extended or adjusted under 35 U.S.C. 154(b) by 0 days.

(21) Appl. No.: 11/315,495

(22) Filed: Dec. 23, 2005

(65) Prior Publication Data

US 2007/0148621 A1  Jun. 28, 2007

(51) Int. Cl.
  *A61C 8/00* (2006.01)
(52) U.S. Cl. ........................................ 433/176; 433/173
(58) Field of Classification Search ......... 433/172–176
  See application file for complete search history.

(56) References Cited

U.S. PATENT DOCUMENTS 5,116,226 A * 5/1992 Linkow ...................... 433/176

5,141,435 A   8/1992 Lillard

* cited by examiner

*Primary Examiner*—Cris Rodriguez
*Assistant Examiner*—Candice C Stokes
(74) *Attorney, Agent, or Firm*—C. J. Husar, Esq.

(57) ABSTRACT

There is disclosed a plurality of extensions for dental implants allowing a dental surgeon to maintain a minimum number of parts in his trays to carry on an effective, successful practice, thus eliminating the need to carry the wide variety of parts offered and carried by surgeons to meet the needs of his practice. The surgeon is only required to carry two different parts, the basic implant body and also the extension that will match that particular implant body. With this combination of elements, the surgeon will be able to place many different implant lengths with a much reduced inventory and corresponding costs to the practitioner.

10 Claims, 1 Drawing Sheet

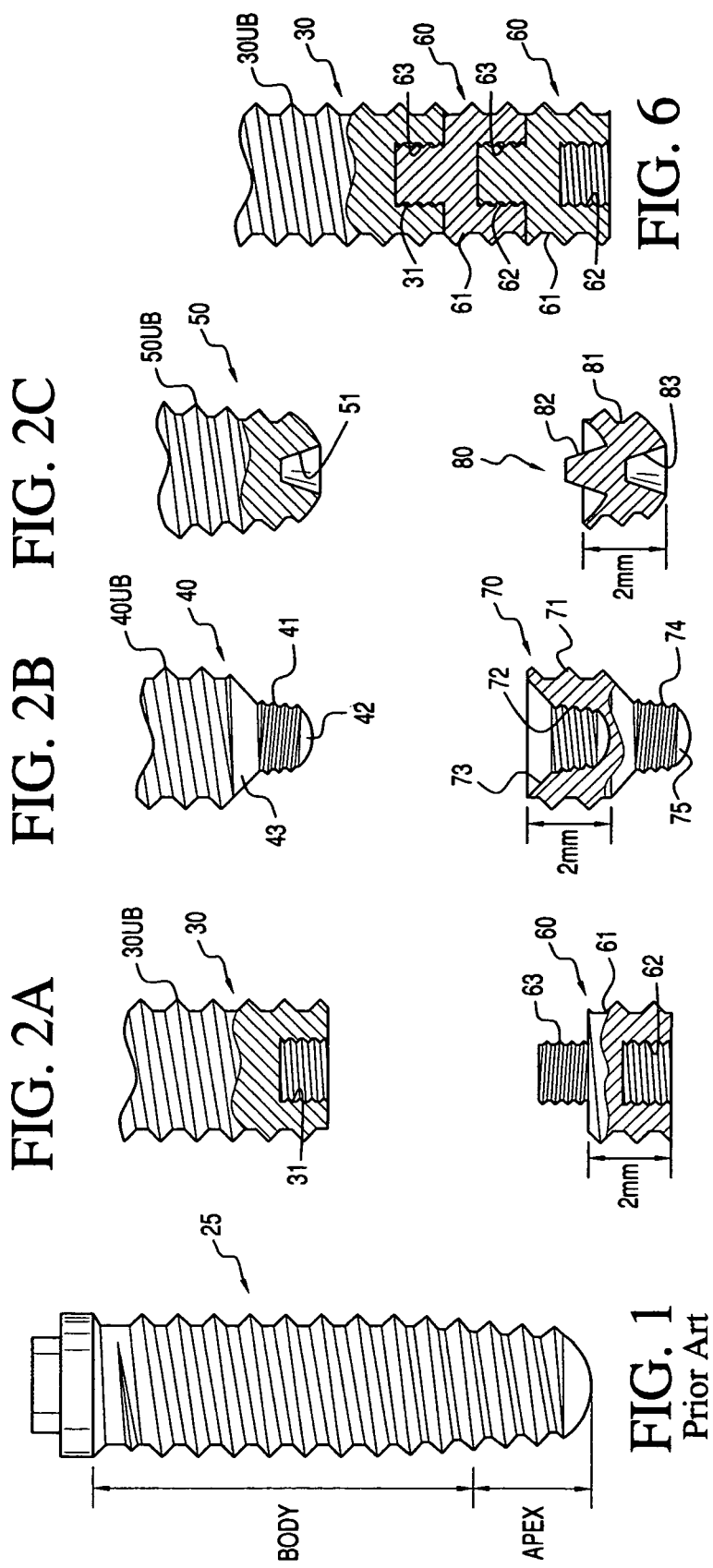

US 7,281,926 B2

MODULAR DENTAL IMPLANTS WITH EXTENSIONS

FIELD OF THE INVENTION

The instant invention relates to a conical endosseous dental implant. More specifically, it relates to a modular extension for a dental implant body. Modern dentistry offers a variety of dental implant manufacturers as well as a variety of dental implant lengths by each of these manufacturers, thus requiring a practitioner to outlay a considerable amount of money to have his tray full of the many varied implants available.

BACKGROUND OF THE INVENTION

Dental implant is an artificial replacement for a tooth root. The dental implant is usually made out of titanium alloy and is surgically and permanently affixed within the bone structure of a patient's jaw to serve as a support for an artificial crown, fixed partial denture or a removable denture. The implant device includes on its coronal end an abutment or a platform to support a releaseably coupled abutment. The abutment extends through the gum tissue to receive a prosthesis.

In order to surgically place a cylindrical dental implant, a hole is drilled into the patient's jawbone and then the implant assembly is inserted into the hole. The implant assembly has on one end of its body a head portion to support the prosthesis, the implant body is used to integrate with the surrounding bone and it ends with a flat or rounded apex, the main function of the implant body is to give support to the prosthesis. In order to do that, it needs to permanently adhere to the surrounding bone in a process called Osseointegration. Increasing the implant body surface area will increase the implant body integration with the surrounding bone.

Before and during implant surgery, the height and width of the available jawbone in the implant site should be assessed and it is recommended to use a longer implant if possible in order to increase the surface area. In the market today implant companies manufacture various lengths of implants to allow the surgeon to place the longest implant possible into the available bone in the implant site.

SUMMARY OF THE INVENTION

The present invention relates to a dental implant system wherein there is a small implant of a single length, i.e. 8-10 mm, that may be extended or lengthened by the addition of one or more modular parts (extensions) to the apical end of the anchoring portion of the implant to give it the required overall length. The implant body has on one end a platform or abutment and on its apical end it can readily accept an extension. The extension part can be connected at one end to the implant apex and on its other end, it can accept another extension.

The surgeon will determine what length of implant is needed in the implant site and he will be able to assemble the required length by using the basic implant body alone or by connecting the basic implant body to one or more extensions at its apex. After the implant length is determined and assembled it will be permanently placed into the hole drilled into the bone at the implant site. By having a dental implant system such as the one described above, the surgeon will be required to maintain only 2 different parts.

OBJECTS OF THE INVENTION

An object of the invention is to provide a dental implant system wherein the number of different parts required for a successful practice is kept to a minimum.

A further object of the invention is to provide a dental implant system wherein many different implant lengths can be placed utilizing only two different parts.

Yet another object of the invention is to provide a dental implant system wherein the costs of operating said system is much less than any other known system.

Still another object of the invention is to provide a dental implant system including a plurality implant apex designs.

A still further object of the invention is to provide a dental implant system wherein a plurality of different implant extensions are provided.

Yet another object of the invention is to provide a dental implant system wherein each implant extension has its own implant apex design.

These and other objects of the invention will become more apparent hereinafter. The instant invention will now be described with reference to the accompanying drawings wherein like reference characters designate the corresponding parts throughout the several views.

BRIEF DESCRIPTION OF THE DRAWINGS

FIG. 1 is an illustration of a known "prior art" dental implant.

FIG. 2A is an illustration of the apex portion of a dental implant.

FIG. 2B is an illustration of the apex portion of a second type of dental implant.

FIG. 2C is an illustration of the apex portion of a third type of dental implant.

FIG. 3 is an illustration of the extension that will fit option I of FIG. 2A.

FIG. 4 is an illustration of the extension that will fit option II of FIG. 2B.

FIG. 5 is an illustration of the extension that will fit option III of FIG. 2C.

FIG. 6 is an illustration of two extensions of FIG. 3 that have been added to the apex shown in FIG. 2A.

DETAILED DESCRIPTION OF THE DRAWINGS

Referring now to FIG. 1, there is shown a typical known "prior art" dental implant 25 currently in use by today's dental surgeons. As shown, the basic implant comprises three main portions, i.e. the head or abutment end is at the uppermost end and it supports the platform which in turn supports the prosthesis (not shown). Next is the centrally located implant body portion, which is followed by the implant apex. It is the apex portion that this invention is most concerned with as can be seen from the remaining drawing figures.

Turning now to FIGS. 2A-2C, there is illustrated three different options of an implant apex design to enable the connection to the extension.

FIG. 2A illustrates the first option, apex 30 shown with only a portion of its upper body portion 30UB illustrated. The details of the upper body portion and the platform of the dental implant have been intentionally omitted since they are not part of the inventive subject matter. As illustrated, apex 30 is provided with a centrally located bore 31 for receiving the externally threaded projection 63 of implant extension 60. Although only a single extension 60, is shown, a plurality of identical extensions 60 may be added to implant apex 30 to give the desired height to the implant after a second extension 60 has been joined by threading externally threaded projection 63 into centrally located bore 62 and mating it therewith.

Referring now to FIG. 2B, which represents the second option apex 40, there is shown an externally threaded shaft 41, with a rounded end 42, and an upper bevel portion 43 with an upper body portion 40 UB.

FIG. 2C is an illustration of the third option apex 50, there is shown an internally locking taper socket 51 for receiving a mating locking taper member 82 of extension 80

FIG. 3 is an illustration of the first option extension 60 with an externally threaded projection 63 that is sized to fit the centrally located bore 31 of apex 30. Additionally, extension 60 has a centrally located bore 62 that is sized to match the threaded projection 63 of another extension 60. As shown, extension 60 has an extension body portion 61 that extends for a length of 2 mm.

FIG. 4 is an illustration of second option extension 70 that includes an extension body portion 71 that extends for a length of 2 mm. Extension body portion includes an internal threaded socket 72 that matches external threaded shaft 41, 42 and a beveled edge 73 that conforms to bevel 43 on apex 40. Further, extension 70 includes an externally threaded shaft 74 and rounded end 75 that conform to socket 72 and can be connected to another extension 70.

FIG. 5 is an illustration of the extension 80 that is used with apex 50 of FIG. 2C. As shown, extension 80 has a body portion 81 of 2 mm the same as the two other extensions. The uppermost portion of extension 80 includes a locking taper 82 that is sized to fit locking taper socket 51 of apex 50 and also on its other end internally locking taper 83, that can be connected to another extension 80.

FIG. 6 is an illustration of the apex shown in FIG. 2A with two extensions 60 joined together and then mated with apex 30.

While the invention has been described in its preferred embodiment, it is to be understood that the words which have been used are words of description rather than words of limitation and that changes may be made within the purview of the appended claims without departing from the full scope or spirit of the invention. Accordingly, the present invention is to be limited only by the appended claims, and not by the foregoing specification.

Having thus described my invention, I claim:

1. A dental implant system having a body of a given length with a prosthesis supporting platform at its uppermost end and an apex at the lowermost end thereof;
    said apex having connecting means for receiving an extension thereon; said extension includes an extension head portion, an extension body portion and an extension apex portion;
    said extension head portion comprising an externally threaded shaft of the same diameter as said centrally located internally threaded bore of said dental implant apex portion;
    said extension body portion including a cylindrical portion having a length of approximately 2 mm; and an extension apex portion therebelow; and;
    said apex connecting means for receiving an extension thereon comprises a connection located at the lowermost end of said apex.

2. A dental implant system as defined in claim 1 wherein said connection at the lowermost end of said apex is internal.

3. A dental implant system as defined in claim 2 wherein said extension includes an extension body having a diameter corresponding to said apex;
    said extension having an externally threaded shaft portion and a centrally located bore whereby a second extension may be threaded into said centrally located bore of said first extension and increase the overall length of said implant body and apex.

4. A dental implant system as defined in claim 1 wherein said connection at the lowermost end of said apex is external.

5. A dental implant system as defined in claim 4 wherein said extension includes an extension head portion, extension body portion and an extension apex portion;
    said extension head comprising a bevel portion that conforms to the bevel of said apex portion;
    said extension body portion includes a cylindrical surface; and
    said extension apex portion includes a bevel immediately below said extension body portion and connecting means for receiving a second extension thereon if so needed.

6. A dental implant system as defined in claim 1 wherein said connecting means comprises a centrally located bore in said apical end of said apex and said extension comprises a body portion having a diameter corresponding to said implant apex and an externally threaded shaft portion projecting from said body portion and receiving means for receiving a second extension.

7. A dental implant system as defined in claim 6 wherein said connecting means for receiving a second extension thereon comprises an internally threaded bore sized to receive a second extension thereon if so needed.

8. A dental implant system as defined in claim 1 wherein said apex connecting means for receiving an extension thereon comprises a bevel portion having its maximum diameter adjacent the body portion of said dental implant and a lesser diameter spaced therefrom; and
    an externally threaded shaft depending from said lesser diameter of said bevel and having a rounded end immediately below said threaded shaft.

9. A dental implant system as defined in claim 1 wherein said apex connecting means for receiving an extension thereon comprises an internally locking taper socket located at the lowermost end of said apex.

10. A dental implant system as defined in claim 1 wherein said extension includes an extension head portion, an extension body portion and an extension apex portion;
    said extension body portion comprising a central body portion;
    an externally projecting locking taper portion extending upward from said extension body forming said extension head portion; and
    an internally locking taper socket portion located immediately below said extension body portion forming extension apex portion whereby said internally locking taper socket can receive another extension therein.

* * * * *